United States Patent
Wang et al.

(10) Patent No.: US 11,557,072 B2
(45) Date of Patent: Jan. 17, 2023

(54) CLUSTERING ALGORITHM-BASED MULTI-PARAMETER CUMULATIVE CALCULATION METHOD FOR LOWER LIMB VASCULAR CALCIFICATION INDEXES

(71) Applicant: AFFILIATED HOSPITAL OF JIANGSU UNIVERSITY, Jiangsu (CN)

(72) Inventors: Zhongqun Wang, Jiangsu (CN); Yue Geng, Jiangsu (CN); Lihua Li, Jiangsu (CN); Chen Shao, Jiangsu (CN); Zhen Sun, Jiangsu (CN); Guangyao Zang, Jiangsu (CN); Lili Zhang, Jiangsu (CN)

(73) Assignee: AFFILIATED HOSPITAL OF JIANGSU UNIVERSITY, Jiangsu (CN)

( * ) Notice: Subject to any disclaimer, the term of this patent is extended or adjusted under 35 U.S.C. 154(b) by 0 days.

(21) Appl. No.: 17/432,094

(22) PCT Filed: May 19, 2021

(86) PCT No.: PCT/CN2021/094611
§ 371 (c)(1),
(2) Date: Aug. 19, 2021

(87) PCT Pub. No.: WO2021/238739
PCT Pub. Date: Dec. 2, 2021

(65) Prior Publication Data
US 2022/0148237 A1  May 12, 2022

(30) Foreign Application Priority Data
May 28, 2020  (CN) .......................... 202010466288.7

(51) Int. Cl.
*G06T 11/00* (2006.01)
*G06V 10/25* (2022.01)
(Continued)

(52) U.S. Cl.
CPC ............ *G06T 11/008* (2013.01); *A61B 6/032* (2013.01); *A61B 6/504* (2013.01); *G06V 10/22* (2022.01);
(Continued)

(58) Field of Classification Search
CPC ....... A61B 6/032; A61B 6/504; G06T 11/008; G06T 2211/424; G06V 10/22;
(Continued)

(56) References Cited

U.S. PATENT DOCUMENTS

2008/0044070 A1* 2/2008 Nie ....................... G06T 7/0012
382/128

FOREIGN PATENT DOCUMENTS

| CN | 103745227 | 4/2014 |
| CN | 106447645 | 2/2017 |
| CN | 111667467 | 9/2020 |

OTHER PUBLICATIONS

"International Search Report (Form PCT/ISA/210) of PCT/CN2021/094611," dated Jul. 27, 2021, pp. 1-5.
(Continued)

*Primary Examiner* — Manuchehr Rahmjoo
(74) *Attorney, Agent, or Firm* — JCIP Global Inc.

(57) ABSTRACT

The present invention discloses a clustering algorithm-based multi-parameter cumulative calculation method for lower limb vascular calcification indexes, including the following steps: firstly carrying out super-pixel segmentation of a CT image, and enabling calcified spots in the CT image to be segmented in each super-pixel region; after the super-pixel segmentation is accomplished, extracting a brightness char-
(Continued)

acteristic value of a super-pixel region where the calcified spots are located by using a Lab color space, and performing edge detection and contour extraction on the calcified spots in the image; and after edge detection and contour extraction, fitting the calcified spots in the image by using a segmented ellipse, and extracting the area of the calcified spots after optimizing an ellipse contour.

7 Claims, 5 Drawing Sheets

(51) Int. Cl.
  *G06V 10/46* (2022.01)
  *G06V 10/75* (2022.01)
  *G06V 10/50* (2022.01)
  *G06V 10/22* (2022.01)
  *G06V 10/36* (2022.01)
  *A61B 6/03* (2006.01)
  *A61B 6/00* (2006.01)

(52) U.S. Cl.
  CPC .............. *G06V 10/25* (2022.01); *G06V 10/36* (2022.01); *G06V 10/473* (2022.01); *G06V 10/50* (2022.01); *G06V 10/76* (2022.01); *G06T 2211/424* (2013.01); *G06V 2201/03* (2022.01)

(58) Field of Classification Search
  CPC ...... G06V 10/25; G06V 10/36; G06V 10/473; G06V 10/50; G06V 10/76; G06V 2201/03
  See application file for complete search history.

(56) References Cited

OTHER PUBLICATIONS

"Written Opinion of the International Searching Authority (Form PCT/ISA/237) of PCT/CN2021/094611," dated Jul. 27, 2021, pp. 1-6.

Cnblogs.com, "calculation of calcification integral in medical image processing," accessed Aug. 2021, Available at: https://www.cnblogs.com/mothe123/p/4481626.html.

* cited by examiner

CLUSTERING ALGORITHM-BASED MULTI-PARAMETER CUMULATIVE CALCULATION METHOD FOR LOWER LIMB VASCULAR CALCIFICATION INDEXES

CROSS-REFERENCE TO RELATED APPLICATION

This application is a 371 of international application of PCT application serial no. PCT/CN2021/094611, filed on May 19, 2021, which claims the priority benefit of China application no. 202010466288.7, filed on May 28, 2020. The entirety of each of the above mentioned patent applications is hereby incorporated by reference herein and made a part of this specification.

TECHNICAL FIELD

The present invention belongs to the technical field of medical image processing, and specifically relates to a clustering algorithm-based multi-parameter cumulative calculation method for lower limb vascular calcification indexes.

BACKGROUND

Diabetic lower extremity arteriosclerosis obliterans, important risk factors of which are diabetes, hypertension, lipid metabolism disorders, and smoking, is a more serious peripheral arterial vascular disease in which diabetes has developed to a certain degree. Due to long-term stimulation of a hyperglycemic factor, diabetic patients often have a more serious degree of peripheral arterial disease in comparison with patients with hypertension, and patients with lower extremity arterial disease are more likely to have higher disability and mortality. Patients with mild conditions may have numbness and chills in the lower limbs while patients with moderate and severe conditions are likely to have intermittent rest pain, and even necrosis that leads to amputation and disability. Due to the complexity of diabetes and the long-term course of the disease, diabetic lower extremity arteriosclerosis obliterans tends to have more extensive and severe lesions than lower extremity arteriosclerosis obliterans caused by other reasons such as more plaques, especially small vascular lesions below a knee being most severe, thus bringing certain difficulty to clinical treatment due to its complexity.

At present, the examination techniques, which also have shortcomings, for lower extremity arteries include ankle-brachial index measurement, arteriography, Color Doppler, CT angiography, magnetic resonance angiography and other methods. The ankle-brachial index measurement cannot judge the degree and nature of vascular stenosis, and there is a false negative rate when calcification is more serious. Arteriography is an invasive examination with high cost and many complications. The examination results of Color Doppler are greatly affected by factors such as the operator's proficiency, and the display of deep blood vessels and adjacent bone blood vessels is poor. The magnetic resonance angiography, although used more and more widely, is low in spatial resolution, has relatively large deviation in diagnosis of small blood vessels, and cannot fully meet the clinical needs. The CT image technology, although used more and more widely, is greatly affected by human factors on judgement results when clinicians mostly assess patients' conditions from imaging results based on personal experience, and therefore, it is necessary to design a more effective method for the CT image, which can output relatively accurate lower limb vascular calcification degree of and effectively prevent human factors from affecting the judgment results through processing of the CT image.

In addition, unlike the distribution of calcified plaques in other arteries of a human body, the branches of lower extremity arteries are more refined and complicated. It is the key point and the difficulty in research at present to correctly obtain vascular calcification indexes of lower limbs as diagnostic accuracy diabetic feet facing amputation is often affected by calcification degree of the calcified plaques in the blood vessels of lower limbs.

SUMMARY

In order to solve the problem that there are no effective calculation methods for lower limb vascular calcification indexes in the prior art, the present invention discloses a clustering algorithm-based multi-parameter cumulative calculation method for lower limb vascular calcification indexes, which gives quantitative values of the lower limb vascular calcification indexes by combining a CT brightness characteristic value obtained by CT image processing of the blood vessels of lower limbs and a calcification area with corresponding cumulative correction coefficient obtained by vascular fluid mechanics study. The values of the lower limb vascular calcification indexes can represent calcification degree of the blood vessels of lower limbs to a great extent, and provide data basis for the risk that diabetic feet face amputation subsequentially.

The technical solution adopted by the present invention is as follows:

step 1, acquiring a CT image of the blood vessels of lower limbs to be analyzed;

step 2, using a linear iterative clustering algorithm to evenly segment the calcified spots in the CT image into each super-pixel region;

step 3, after accomplishing the super-pixel segmentation, extracting a brightness characteristic value of a super-pixel region where the calcified spots are located by using a Lab color space;

step 4, performing edge detection and contour extraction on the calcified spots in the CT image, fitting the calcified spots in the processed image by using a segmented ellipse and optimizing to obtain a radius of the calcified spots, thereby calculating the area of the calcified spots; and step 5, obtaining a judgment value of the calcification degree in the CT image according to $Cal = k \cdot \rho \cdot S$, where $\rho$ is a CT brightness characteristic value, $S$ is an area of the calcified spots, and $k$ is a cumulative correction coefficient.

Further, the step 2 of performing super-pixel segmentation on the CT image is as follows:

step 2.1, performing even super-pixel segmentation on the acquired original CT image of the blood vessels of the lower limbs, setting X pixels in the original CT image of the blood vessels of the lower limbs, segmenting the original CT image of the blood vessels of the lower limbs into K regions, where each super-pixel has $$\frac{X}{K}$$

pixels;

step 2.2, presetting an interval between an initial clustering center C and an initial clustering center C;

step 2.3, searching pixels close to C in the field of clustering center C based on a Euclidean distance, and classifying the pixels into one category;

step 2.4, calculating an average eigenvector value of all pixels in the K super-pixel regions, performing next clustering based on the average eigenvector value, iteratively updating the clustering center, and iterating again until the end of the iteration; and step 2.5, segmenting the iterated super pixels to obtain the super-pixel regions.

Further, the step 3 of extracting the brightness characteristic value of the super-pixel region where the calcified spots are located is as follows:

step 3.1, extracting a brightness channel L in Lab and representing brightness characteristic $$L = 116 f\left(\frac{Y}{Y_0}\right) - 16$$

of the CT image of the blood vessels of the lower limbs to obtain a brightness image $L_0$ of the CT image of the blood vessels of the lower limbs, where Y is an intermediate variable, $Y_0$ is a gray value of white defined by the CIE standard, and $f$ is a correction function; and step 3.2, based on a brightness map $L_0$, extracting the brightness characteristic value of the super-pixel region where the calcified spots are located.

Further, the step 3.2 of extracting the brightness characteristic value is as follows:

step 3.2.1, using Gaussian-filtering ½ down-sampling to process $L_0$ to obtain an image $L_1$, $L_1$=subsample(lpfilter ($L_0$)), where subsample( ) is a down-sampling function and lpfilter( ) is a frequency domain filter function;

step 3.2.2, extracting the maximum brightness pixel point A(x,y) in the super-pixel region subjected to Gaussian filtering, and obtaining a sum $$P_y(x) = \sum_{y=y_1}^{y_2} f(x, y)$$

of the gray values of all pixels in the super-pixel region, where (x, y) are pixel coordinates, y∈($y_1$, $y_2$), x∈($x_1$, $x_2$) and $y_1$ and $y_2$ are coordinate values in the y-axis direction in the super-pixel region, $x_1$ and $x_2$ are coordinate values in the x-axis direction in the super-pixel region, $f$(x,y) is pixel values at (x,y), $P_y$(x) is a cumulative sum of the gray values of the column vector pixels at the x, and a sum of grey values of all pixels in the entire super-pixel region is obtained by $$P = \sum_{x=x_1}^{x_2} P_y(x);$$

and step 3.2.3, obtaining a cumulative sum of the gray values of all pixels in the entire super-pixel region as the CT brightness value.

Further, the process of extracting the calcified spots by edge detection and contour extraction is as follows:

step 4.1.1, using a Gaussian filter to preprocess the image;

step 4.1.2, using a sobel operator to calculate a gradient size and a direction of each pixel point in the filtered image;

step 4.1.3, selecting edge points based on the gradient intensity comparison of the pixels, keeping the edge points while the gradient intensity of certain pixel is greater than that of another two pixels in a positive and negative gradient direction, otherwise, suppressing the pixel; and step 4.1.4, comparing the edge points obtained in the previous step with an upper threshold, and then screening the edge points; if the upper threshold is less than the edge points, keeping the point and setting the changed point as the first edge point; then searching whether or not a neighboring point of this point is less than the upper threshold, repeating this process and connecting all the points greater than the upper threshold.

Further, the method of fitting by the segmented ellipse is as follows:

step 4.2.1, randomly segmenting the obtained contour into n segments;

step 4.2.2, randomly selecting 12 non-repetitive points in each segment of the contour, and using the least squares method to fit n candidate ellipses;

step 4.2.3, setting a judgment threshold value $l_0$, comparing a distance $l_i$ between the point ($x_i$, $y_i$) and the candidate ellipse contour with a judgment threshold value $l_0$; if $l_i$ is greater than $l_0$, discarding the changed point and not recording; if $l_i$ is smaller than or equal to $l_0$, keeping the changed point, recording as one, and summarizing the relevant parameters of the point to obtain a data set $V_i$=($x_{ic}$,$y_{ic}$,$a_i$,$b_i$, $\theta_i$,$n_i$,$s_i$), where the circle center of the candidate ellipse is ($x_{ic}$, $y_{ic}$), a semi-major axis is $a_i$, a semi-minor axis is $b_i$, a rotation angle is $\theta_i$, $s_i$ represents a serial number of each segment, and $n_i$ is the number of contour segments; and repeating the above comparison process until all points on the candidate ellipse contour are compared, summing up all the kept data set of the M points to obtain V={$V_i$=($x_{ic}$,$y_{ic}$, $a_i$,$b_i$,$\theta_i$,$n_i$,$s_i$)|i=1, 2, . . . , M}, where the one with the most votes is the fitted result.

Further, the ellipse contour is obtained by an active contour model to obtain the area of the calcified spots;

step 4.3.1, using a snake model to give a 2D parameter closed curve near the region of interest, and by minimizing the energy functional, deforming the closed curve in the image and continuously approximating the target contour, receiving the final evolution results as the target contour, and expressing a contour curve energy function as follows:

$$E^*_{snake} = \int_0^1 E_{snake}(v(s))ds = \int_0^1 E_{int}(v(s)) + E_{ext}(v(s))ds$$

where, $E_{snake}$(v(s)) is curve energy, v(s) is a parameter equation of snake contour, $E_{int}$ is internal energy of the curve, which determines the smoothness and continuity of the curve; $E_{ext}$ is energy given to the curve by the outside, which makes the curve move towards a characteristic direction of the target, and s is an independent variable describing the boundary;

and step 4.3.2, using the least-square circle fitting method to re-fit the circle, and getting the center of the circle through a weighting function of the coordinates of the edge points on all the circles, that is, the centers (X, Y) of the calcified spots, where $$X = \frac{1}{N}\sum_{i=1}^{N} x_i, Y = \frac{1}{N}\sum_{i=1}^{N} y_i$$

and the diameters $$D = \frac{2}{N} \sum_{i=1}^{N} \sqrt{(x_i - X)^2 + (y_i - Y)^2}$$

of the calcified spots are calculated, $x_i$ and $y_i$ respectively represent the coordinates of certain point on the contours of the calcified spots, and N is the number of points on the contours of the calcified spots; and finally getting the area of the calcified spots.

Further, the cumulative correction coefficient $k=k_h*k_w*k_o*k_p$, $k_h$ is a cumulative score of stenosis; $k_w$ is a cumulative score of wall shear stress w of the lower extremity arteries; $k_o$ is a cumulative score of an oscillating shear index o of the lower extremity arteries; $k_p$ is a cumulative score of wall shear stress p of the lower extremity arteries;

the cumulative calculation standard for lower extremity arterial stenosis is as follows: according to the lumen area of the lower extremity arteries, it is divided into four grades: I. under lumen diameter reduction of 1%-25%, cumulative stenosis score $k_h$ is 1 point. II. under lumen diameter reduction of 25%-50%, stenosis cumulative score $k_h$ is 2 points, III. under lumen diameter reduction 51%-75%, stenosis cumulative score $k_h$ is 3 points, IV. under lumen diameter reduction 76%-100%, stenosis cumulative score $k_h$ is 4 points, where the method of collecting stenosis data is as follows: collecting the maximum value of the vascular stenosis $h_{max}$ and the average value $\bar{h}$ of the stenosis, in the segment with calcified plaques, of the lower extremity artery, and determining the value $\hat{h}$ of vascular stenosis of this segment according to $\hat{h}=ah_{max}+b\bar{h}$, where a and b are constant coefficients.

The cumulative calculation standard for wall shear stress w of lower limb arteries is as follows: wall shear stress in an arterial system is generally (10-70) dynes/cm$^2$, and when wall shear stress w is (0-4) dynes/cm$^2$, the cumulative score $k_w$ is 3 points, when the wall shear stress w is (5-10) dynes/cm$^2$, the cumulative score $k_w$ is 2 points, and when the wall shear stress w is (11-70) dynes/cm$^2$, the cumulative score $k_w$ is 1 point.

The accumulative calculation standard for the oscillating shear index o of the lower limb arteries is as follows: the normal range of the index is 0-0.5, when the oscillating shear index is lower than 0.2, the cumulative score $k_o$ is 3 points, the cumulative score $k_o$ is 2 points when the oscillating shear index is between 0.2 and 0.3, and when the oscillating shear index is between 0.3 and 0.5, the cumulative score $k_o$ is 1 point.

The accumulative calculation standard for wall shear stress p of lower limb arteries is as follows: a normal range of indicators is systolic blood pressure of 90-140 mmHg, diastolic blood pressure of 60-90 mmHg; when the systolic blood pressure is lower than 90 mmHg and the diastolic blood pressure is lower than 60 mmHg, the cumulative score $k_p$ is 3 points; when the systolic blood pressure is between 90-140 mmHg and the diastolic blood pressure is between 60-90 mmHg, the cumulative score $k_p$ is 2 points; and when the systolic blood pressure is higher than 140 mmHg and the diastolic blood pressure is higher than 90 mmHg, the cumulative score $k_p$ is 1 point.

The present invention has the following beneficial effects:

Firstly, the clustering algorithm-based multi-parameter cumulative calculation method for lower limb vascular calcification indexes disclosed by the present invention firstly performs super-pixel segmentation on the CT image of the blood vessels of the lower limbs in a process of processing the CT image of the blood vessels of the lower limbs, so that on one hand, the pixels can be aggregated together to form multiple sub-region blocks with regular shapes and consistent local structures, and thus, overall expression of image local factures and structural information is realized, excessive data are avoided, processing speed is increased, and data dimensions are reduced by super pixels; on the other hand, the linear iterative clustering algorithm is used to calculate the average value of the features in the super-pixel region to replace the pixel value in the region, which can keep effective information to the greatest extent and reduce noises.

Secondly, in the process of extracting the brightness characteristic value of the super-pixel region where the calcified spots are located by using a Lab color space, a low-pass filter and sub-sampling operation are firstly used layer by layer on the original image $L_0$ to obtain an spatial-scale-transform brightness intensity map of the original image $L_0$, which can enhance the edge of the salient area of the image; then, the sum of the gray values of all pixels in the super pixel area is calculated according to the pixel point with the maximum brightness in the super pixel region, and the CT brightness value can be obtained from the Lab color space by using pixel gray value integral.

Thirdly, when the calcified area in the CT image is extracted, a Canny operator is used to perform edge detection and contour extraction on the calcified spots in the image, and a Gaussian filter is used to preprocess the image to reduce the effect of noises; non-maximum suppression is used to make the edge have an accurate response, and the accuracy of the target is improved by edge detection on a correct position. Hysteresis threshold processing detection is used to connect edge points, and remove false edges, so that edge positioning precision is improved.

Fourthly, the present adopts an active contour model to optimize the ellipse contour, that is, the snake model is used to deform the contour under the action of internal and external forces, and the external energy attracts the active contour to continuously approach the target contour, and is finally evolved to be received as the target contour, where the contour which is evolved through the snake model curve and is refitted is closer to the real contour.

And fifthly, the clustering algorithm-based multi-parameter cumulative calculation method for lower limb vascular calcification indexes gives quantitative values of the lower limb vascular calcification indexes by combining a CT brightness characteristic value obtained by CT image processing of the blood vessels of lower limbs and a calcification area with corresponding cumulative correction coefficient obtained by vascular fluid mechanics study. The values of the lower limb vascular calcification indexes can represent calcification degree of the blood vessels of lower limbs to a great extent, provide data basis for the risk that diabetic feet face amputation subsequentially, and effectively reduce errors caused by experienced judgment. Besides, the calcification degree is obtained by processing the CT image, the influence of human judgment factor is avoided and accuracy is improved.

DETAILED DESCRIPTION

Figure 1:
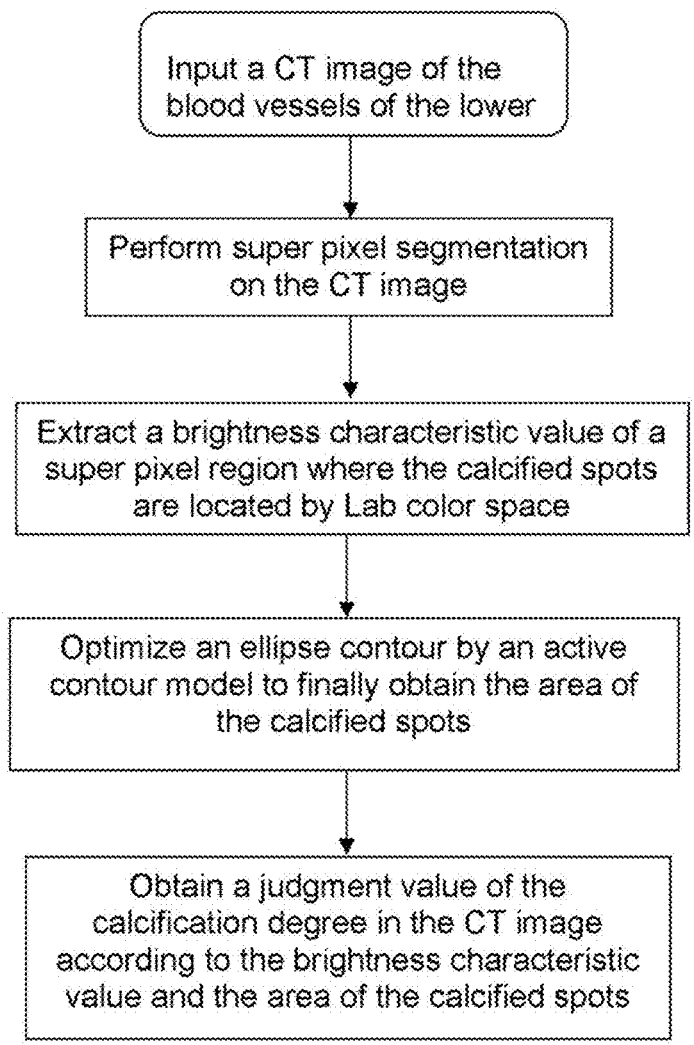
FIG. 1 is flow chart of the method of the present invention.
Figure 2:
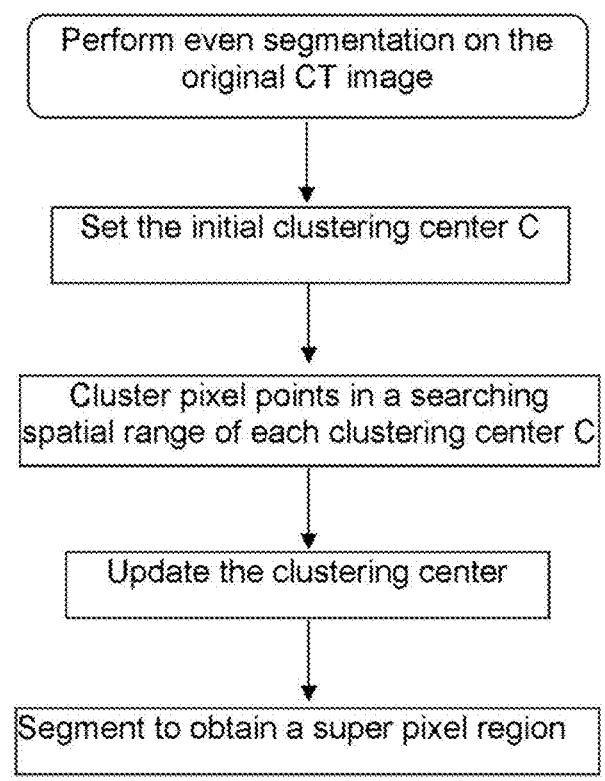
FIG. 2 is flow chart of dividing the super pixel region.
Figure 3:
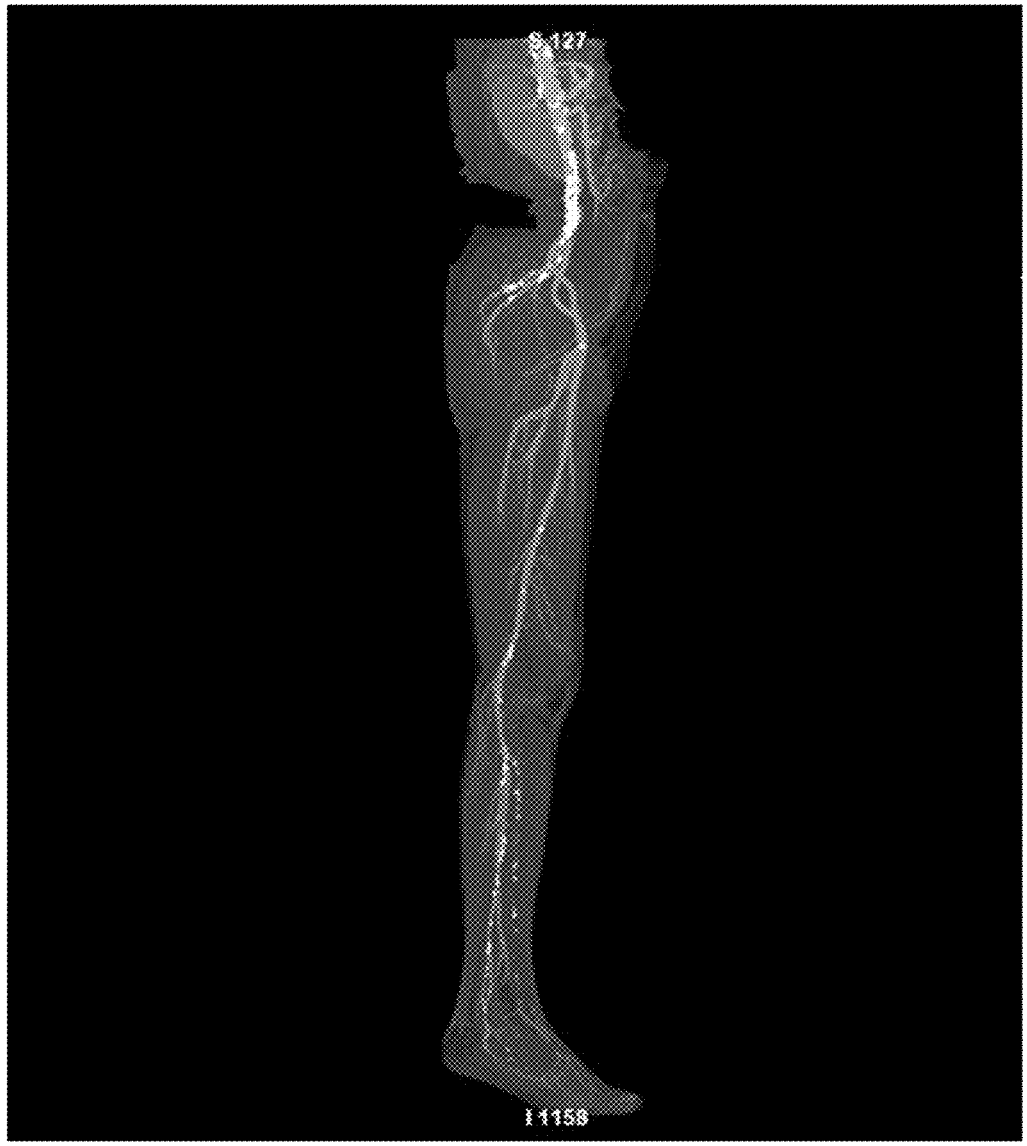
FIG. 3 is a CT image of the lower limbs of a diabetic patient.

In order to make the objective, technical solution and advantages of the present invention clear, the present invention is further illustrated in detail in combination with the accompanying drawings and embodiments hereinafter. It should be understood that specific embodiments described herein are only used for explaining the present invention, instead of limiting the present invention.

Step 1, a CT image of the blood vessels of lower limbs of a diabetic patient was acquired by detecting instruments such as a CT to obtain a CT image of the blood vessels of lower limbs to be analyzed;

step 2, a linear iterative clustering algorithm (SLIC) was used to evenly segment the calcified spots in the CT image into each super-pixel region as follows:

step 2.1, X pixels in the original CT image of the blood vessels of the lower limbs were set, K initial super pixels were set, and the original CT image was evenly segmented, where each cut each super-pixel region had $$\frac{X}{K}$$

pixels;

step 2.2, an interval between an initial clustering center C and an initial clustering center C was preset;

step 2.3, pixels close to C in the field of clustering center C were searched based on a Euclidean distance, and the pixels were classified into one category until all pixel points in the field where each clustering center C was located were segmented;

step 2.4, an average eigenvector value of all pixels in the K super-pixel regions was calculated, next clustering was performed based on the average eigenvector value, the clustering center was iteratively updated and iterated again until the end of the iteration;

step 2.5, the iterated super pixels were segmented to obtain the super-pixel regions.

step 3, after accomplishing the super-pixel segmentation, a brightness characteristic value of a super-pixel region where the calcified spots were located was extracted by using a Lab color space as follows:

step 3.1, a brightness channel L in Lab was extracted and brightness characteristic $$L = 116 f\left(\frac{Y}{Y_0}\right) - 16$$

of the CT image of the blood vessels of the lower limbs was represented to obtain a brightness image $L_0$ of the CT image of the blood vessels of the lower limbs, where Y was an intermediate variable, $Y_0$ was a gray value of white defined by the CIE standard, and $f$ was a correction function; and step 3.2, based on a brightness map $L_0$ of the L channel, the brightness characteristic value of the super-pixel region where the calcified spots were located was extracted as follows:

step 3.2.1, brightness map $L_0$ of the L channel was read, $L_0$ was used as the original image, and the image $L_1$ was got through Gaussian filtering ½ down-sampling, $L_1$=subsample(lpfilter($L_0$)), where subsample( ) was a down-sampling function; lpfilter( ) was a frequency domain filter function; an image $L_1$ with $L_0$ intensity could be obtained after frequency domain filtering and down-sampling operations were performed on $L_0$, and the edges of the salient areas of the processed image were effectively enhanced;

step 3.2.2, the maximum brightness pixel point A(x,y) in the super-pixel region in the brightness-enhanced image $L_1$ was extracted, and a sum $$P_y(x) = \sum_{y=y_1}^{y_2} f(x, y)$$

of the gray values of all pixels in the super-pixel region was obtained, where (x, y) were pixel coordinates, $y \in (y_1, y_2)$, $x \in (x_1, x_2)$ and $y_1$ and $y_2$ were coordinate values in the y-axis direction in the super-pixel region, $x_1$ and $x_2$ were coordinate values in the x-axis direction in the super-pixel region, $f(x,y)$ was pixel values at (x,y), $P_y(x)$ was a cumulative sum of the gray values of the column vector pixels at the x, and a sum of grey values of all pixels in the entire super-pixel region was obtained by $$P = \sum_{x=x_1}^{x_2} P_y(x);$$

and step 3.23, a cumulative sum of the gray values of all pixels in the entire super-pixel region was obtained as the CT brightness value.

step 4, a calcified area in the CT image was extracted, and calcified spots distributed at the lower limbs of the patients could be shown as spots with unsmooth peripheries from the CT image, and thus, the process of extracting the calcified area from the image was as follows:

step 4.1, the process of extracting the calcified spots by edge detection and contour extraction was as follows:

step 4.1.1, A Gaussian filter was used to preprocess the image for smoothing the image and filtering noises;

step 4.1.2, a sobel operator was used to calculate a gradient size and a direction of each pixel point in the filtered image;

step 4.1.3, edge points were selected based on the gradient intensity comparison of the pixels, the edge points while the gradient intensity of certain pixel is greater than that of another two pixels in a positive and negative gradient direction were kept, otherwise, the pixel point was suppressed to 0; and the edge points could generate accurate response through the selection process, so that accuracy of extracting the edge points was improved; and step 4.1.4, the edge points obtained in the previous step were compared with a set upper threshold, and then the edge points were screened; if the upper threshold is less than the edge points, the point was kept and the changed point was set as the first edge point; then whether or not a neighboring point of this point is less than the upper threshold was searched, this process was repeated and all the points greater than the upper threshold were connected; and false edges were removed, so that edge positioning precision was improved.

Step 4.2, the method of fitting by the segmented ellipse was follows:

step 4.2.1, the obtained contour obtained in the previous step was randomly segmented into n segments, n∈[8, 12], where n was an even number within the range;

step 4.2.2, 12 non-repetitive points in each segment of the contour were randomly selected, and the least squares method was used to fit n candidate ellipses;

step 4.2.3, a judgment threshold value $l_0$ was set, a distance $l_i$ between the point $(x_i, y_i)$ and the candidate ellipse contour was compared with a judgment threshold value $l_0$; if $l_i$ was greater than $l_0$, the changed point was discarded and not recorded; if $l_i$ was smaller than or equal to $l_0$, the changed point was kept and recorded as one, and the relevant parameters of the point to obtain a data set $V_i=(x_{ic},y_{ic},a_i,b_i,\theta_i,n_i,s_i)$ were summarized, where the circle center of the candidate ellipse was $(x_{ic}, y_{ic})$, a semi-major axis was $a_i$, a semi-minor axis was $b_i$, a rotation angle was $\theta_i$, $s_i$ represented a serial number of each segment, and $n_i$ was the number of contour segments; and the above comparison process was repeated until all points on the candidate ellipse contour were compared, all the kept data set of the M points was summed up to obtain $V=\{V_i=(x_{ic},y_{ic},a_i,b_i,\theta_i,n_i,s_i)|i=1, 2, \ldots, M\}$, where the one with the most votes was determined as the candidate circle. The present invention used the segmented ellipse fitting to effectively reduce the probability of fitting an incorrect ellipse and improved the accuracy.

step 4.3, an ellipse contour was optimized by an active contour model to finally obtain the area of the calcified spots;

step 4.3.1, a snake model was used to give a 2D parameter closed curve near the region of interest, and by minimizing the energy functional, the closed curve was deformed in the image and continuously approximate the target contour, the final evolution results were received as the target contour, and a contour curve energy function was expressed as follows:

$$E^*_{snake}=\int_0^1 E_{snake}(v(s))ds=\int_0^1 E_{int}(v(s))+E_{ext}(v(s))ds$$

Where, $E_{snake}(v(s))$ was curve energy, $v(s)$ was a parameter equation of snake contour, $E_{int}$ was internal energy of the curve, which determined the smoothness and continuity of the curve; $E_{ext}$ was energy given to the curve by the outside, which made the curve move towards a characteristic direction of the target, and s was an independent variable describing the boundary;

and step 4.3.2, the least-square circle fitting method was used to re-fit the circle, and the center of the circle was got through a weighting function of the coordinates of the edge points on all the circles, that is, the centers (X, Y) of the calcified spots, where $$X = \frac{1}{N}\sum_{i=1}^{N} x_i, Y = \frac{1}{N}\sum_{i=1}^{N} y_i$$

and the diameters $$D = \frac{2}{N}\sum_{i=1}^{N} \sqrt{(x_i - X)^2 + (y_i - Y)^2}$$

of the calcified spots was calculated, $x_i$ and $y_i$ respectively represented the coordinates of certain point on the contours of the calcified spots, and N was the number of points on the contours of the calcified spots; and the area of the calcified spots was finally got.

Figure 4:
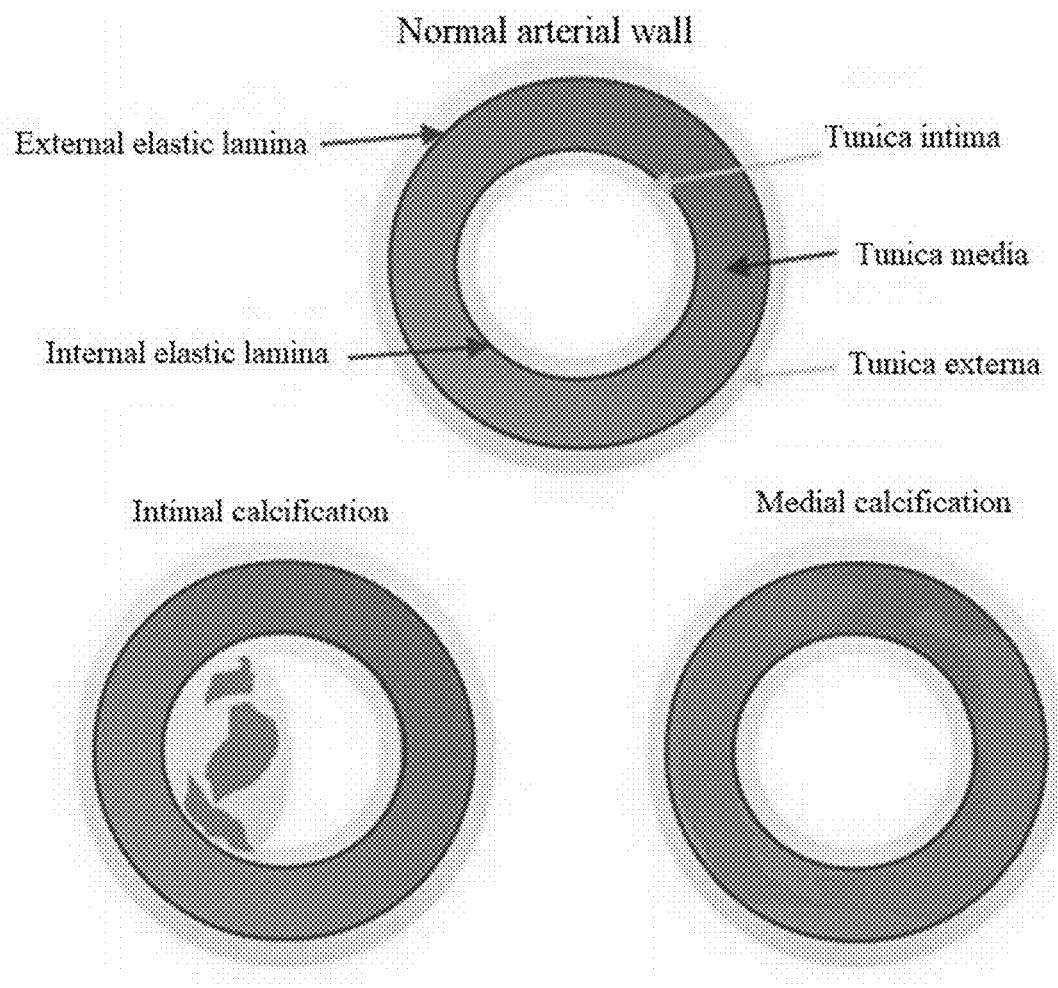
FIG. 4 is a schematic diagram of medial calcification and intimal calcification of arterial blood vessels.
Figure 5:
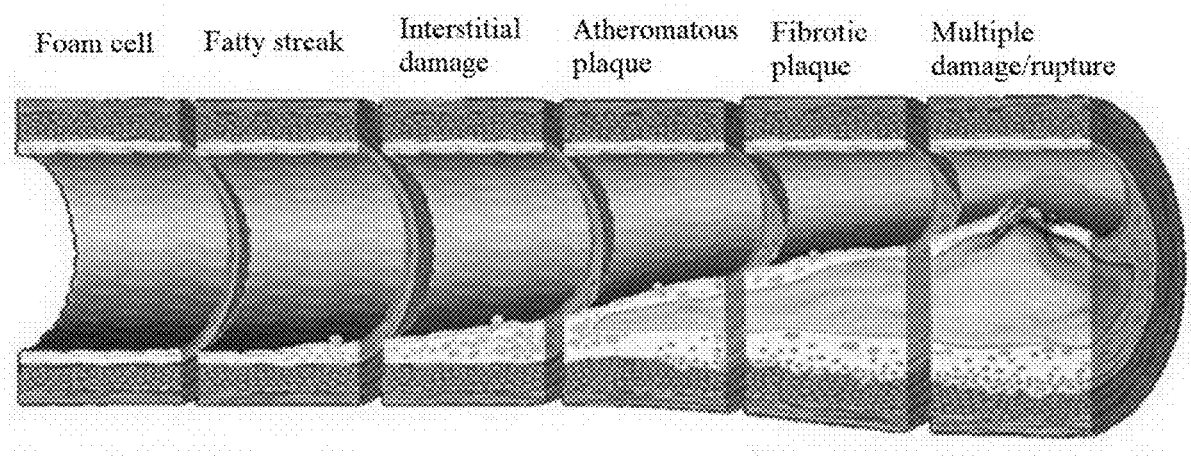
FIG. 5 is a schematic diagram of the progression of atherosclerosis.

Step 5, the CT brightness value ρ and the area S of the calcification spots obtained in the above steps 3 and 4 were substituted into Cal=k·ρ·S to obtain a judgment value of the calcification degree in the CT image, where k was the cumulative correction coefficient, and the calcification indexes not only related to the areas S of the calcified spots in the CT image, the brightness of the calcified spots, and the stenosis, but also closely related to the wall shear stress w, the oscillating shear index o, and the wall pressure p. The blood vessels which were 4 cm long in the region where the calcified spots were located were intercepted. The cumulative correction coefficient k was used to correct the calcification degree, the dynamics of blood flow changed significantly in the stenosis section after stenosis appeared in the arterial lumen as types of calcification in the lower extremity arteries included intimal calcification and medial calcification, and according to the calcified spots in the CT image, it was impossible to directly distinguish the intimal calcification or medial calcification as shown in FIG. 4 and FIG. 5, but intimal calcification could easily cause stenosis of the arterial lumen. Therefore, in the present invention by increasing the cumulative correction coefficient k to comprehensively calculate the CT brightness value ρ and the area S of the calcified spots, so that a more accurate judgment value of the calcification degree was obtained, and the judgment value of the calcification index in the CT image was obtained according to Cal=k·ρ·S;

where, the cumulative calculation of the area S of calcified plaques of the lower extremity artery could be directly obtained by fitting the calcified spots in the image processed using the segmented ellipse and performing optimization processing to obtain the radius of the calcified spots, and then calculating the area of the calcified spots; or the cumulative calculation was directly given by the scoring standard: the size of the calcified plaque area on the anterior and posterior walls of the lower extremity arteries was divided into four grades: I, when there was no calcification, scored 0; II, when calcification range was less than ⅓ of the arterial wall length, scored 1; III. When calcification range was ⅓ to ⅔ of the arterial wall length, scored 2; IV. When calcification range was greater than ⅔ of the arterial wall length, scored 3. The blood vessels of the lower limbs were divided into the upper and lower sections by taking the middle of shanks as boundary lines, including: proximal posterior tibial artery, distal tibial artery, proximal anterior tibial artery, distal tibial artery, proximal peroneal artery, and distal peroneal artery end.

The brightness value ρ of the super pixel region where the calcification spots were located can be directly obtained by extracting the CT brightness characteristic value of the super pixel region where the calcification spots were located through the Lab color space in the clustering algorithm.

The above cumulative correction coefficient could be obtained according to the following calculation formula: $k=k_h*k_w*k_o*k_p$, where $k_h$ was the cumulative score of stenosis; $k_w$ was the cumulative score of the wall shear stress w of the lower extremity arteries; $k_o$ was the cumulative score of the oscillating shear index o of the lower extremity arteries; $k_p$ was the cumulative score of wall shear stress p of the lower extremity arteries; and the calculation standard of specific cumulative correction coefficient k was as follows:

the cumulative calculation standard for lower extremity arterial stenosis was as follows: according to the lumen area of the lower extremity arteries, it was divided into four grades: I. under lumen diameter reduction of 25%-50%, cumulative stenosis score $k_h$ was 1 point; II. under lumen diameter reduction of 25%-50%, stenosis cumulative score $k_h$ was 2 points; III. under lumen diameter reduction 51%-75%, stenosis cumulative score $k_h$ was 3 points; IV. under lumen diameter reduction 76%-100%, stenosis cumulative score $k_h$ was 4 points, where the method of collecting stenosis data was as follows: collecting the maximum value of the vascular stenosis $h_{max}$ and the average value $\bar{h}$ of the stenosis, in the segment with calcified plaques, of the lower extremity artery, and determining the value $\hat{h}$ of vascular stenosis of this segment according to $\hat{h}=ah_{max}+b\bar{h}$, where a and b were constant coefficients.

The cumulative calculation standard for wall shear stress w of lower limb arteries was as follows: wall shear stress in an arterial system was generally (10-70) dynes/cm$^2$, and when wall shear stress w was (0-4) dynes/cm$^2$, the cumulative score $k_w$ was 3 points, when the wall shear stress w was (5-10) dynes/cm$^2$, the cumulative score $k_w$ was 2 points, and when the wall shear stress w was (11-70) dynes/cm$^2$, the cumulative score $k_w$ was 1 point.

The accumulative calculation standard for the oscillating shear index o of the lower limb arteries was as follows: the normal range of the index was 0-0.5, when the oscillating shear index was lower than 0.2, the cumulative score $k_o$ was 3 points, and when the oscillating shear index was between 0.2 and 0.3, the cumulative score $k_o$ was 2 points, the cumulative score $k_o$ was 1 point when the oscillating shear index was between 0.3 and 0.5.

The accumulative calculation standard for wall shear stress p of lower limb arteries was as follows: a normal range of indicators was systolic blood pressure of 90-140 mmHg, diastolic blood pressure of 60-90 mmHg; when the systolic blood pressure was lower than 90 mmHg and the diastolic blood pressure was lower than 60 mmHg, the cumulative score $k_p$ was 3 points; when the systolic blood pressure was between 90-140 mmHg and the diastolic blood pressure was between 60-90 mmHg, the cumulative score $k_p$ was 2 points; and when the systolic blood pressure was higher than 140 mmHg and the diastolic blood pressure was higher than 90 mmHg, the cumulative score $k_p$ was 1 point.

The clustering algorithm-based multi-parameter cumulative calculation method for lower limb vascular calcification indexes of the present invention does not directly aim to obtain the diagnosis results or health status of diabetic foot disease, but only obtains information as the intermediate result from the living human body, which provides intermediate data support for diagnosis of the diabetic foot disease, and does not belong to the category of disease diagnosis.

The embodiment discussed above is merely for describing the technical concepts and features of the present invention, the objectives are that those skilled in this art could understand the content of the present invention and implement therefrom, limitation to the patent scope of the present invention cannot be made only by this embodiment, that is to say, any equivalent variations or modifications in accordance with the spirit disclosed by the present invention shall be contemplated as being within the patent scope of the present invention.

What is claimed is:

1. A clustering algorithm-based multi-parameter cumulative calculation method for lower limb vascular calcification indexes, comprising the following steps:

step 1, acquiring a CT image of blood vessels of lower limbs to be analyzed;

step 2, using a linear iterative clustering algorithm to evenly segment calcified spots in the CT image into each of super-pixel regions, wherein a step of performing a super-pixel segmentation on the CT image is as follows:

step 2.1, performing even the super-pixel segmentation on an acquired original CT image of the blood vessels of the lower limbs, setting X pixels in an original CT image of the blood vessels of the lower limbs, segmenting the original CT image of the blood vessels of the lower limbs into K regions, wherein each of super-pixels has $$\frac{X}{K}$$

pixels;

step 2.2, presetting an initial clustering center C and, presetting an interval between the initial clustering center C;

step 2.3, searching pixels close to the initial clustering center C in a field of the initial clustering center C based on a Euclidean distance, and classifying the pixels into one category;

step 2.4, calculating an average eigenvector value of all of the pixels in K super-pixel regions, performing next clustering based on the average eigenvector value, iteratively updating a clustering center, and iterating again until the end of the iteration; and step 2.5, segmenting the super-pixels, which have been iterated, to obtain the super-pixel regions;

step 3, after accomplishing the super-pixel segmentation, extracting a brightness characteristic value of a super-pixel region where the calcified spots are located by using a Lab color space;

step 4, performing an edge detection and a contour extraction on the calcified spots in the CT image, fitting and optimizing the calcified spots in the CT image by using a segmented ellipse to obtain a radius of the calcified spots, thereby calculating an area of the calcified spots; and step 5, obtaining a judgment value of a calcification degree in the CT image according to Cal=k·ρ·S, where ρ is a CT brightness characteristic value, S is an area of the calcified spots, and k is a cumulative correction coefficient.

2. The clustering algorithm-based multi-parameter cumulative calculation method for the lower limb vascular calcification indexes according to claim 1, wherein the step 3 of extracting the brightness characteristic value of the super-pixel region where the calcified spots are located is as follows:

step 3.1, extracting a brightness channel L in Lab color space and representing brightness characteristic $$L = 116 f\left(\frac{Y}{Y_0}\right) - 16$$

of the CT image of the blood vessels of the lower limbs to obtain a brightness image $L_0$ of the CT image of the blood vessels of the lower limbs, wherein Y is an intermediate variable, $Y_0$ a gray value of white defined by the CIE standard, and $f$ is a correction function; and step 3.2, based on the brightness image $L_0$ of the brightness channel L, extracting the brightness characteristic value of the super-pixel region where the calcified spots are located.

3. The clustering algorithm-based multi-parameter cumulative calculation method for the lower limb vascular calcification indexes according to claim 2, wherein the step 3.2 of extracting the brightness characteristic value is as follows:

step 3.2.1, using Gaussian-filtering ½ down-sampling to process $L_0$ to obtain an image $L_1$, $L_1$=subsample(lpfilter($L_0$)), where subsample was a down-sampling function; lpfilter is a frequency domain filter function;

step 3.2.2, extracting a maximum brightness pixel point A(x,y) in the super-pixel region subjected to Gaussian filtering, and obtaining a sum $$P_y(x) = \sum_{y=y_1}^{y_2} f(x, y)$$

of gray values of all of pixels in the super-pixel region, wherein (x, y) are pixel coordinates, $y \in (y_1, y_2)$, $x \in (x_1, x_2)$ and $y_1$ and $y_2$ are coordinate values in the y-axis direction in the super-pixel region, $x_1$ and $x_2$ are coordinate values in the x-axis direction in the super-pixel region, $f(x,y)$ is pixel values at (x,y), $P_y(x)$ is a cumulative sum of the gray values of column vector pixels at the x, and a sum of the gray values of all of the pixels in an entire super-pixel region is obtained by $$P = \sum_{x=x_1}^{x_2} P_y(x);$$

and step 3.2.3, obtaining a cumulative sum of the gray values of all of the pixels in the entire super-pixel region as a CT brightness value.

4. The clustering algorithm-based multi-parameter cumulative calculation method for the lower limb vascular calcification indexes according to claim 1, wherein a process of extracting the calcified spots by the edge detection and the contour extraction is as follows:

step 4.1.1, using a Gaussian filter to preprocess an image;

step 4.1.2, using a sobel operator to calculate a gradient size and a direction of each of pixel points in a filtered image;

step 4.1.3, selecting edge points based on a gradient intensity comparison of pixels, keeping the edge points while the gradient intensity of a pixel is greater than that of another two of the pixels in a positive gradient direction and a negative gradient direction, otherwise, suppressing the pixel; and step 4.1.4, comparing the edge points obtained in the previous step with an upper threshold, and then screening the edge points; if the upper threshold is less than the edge points, keeping a point and setting a changed point as a first edge point; then searching whether or not a neighboring point of the point is less than the upper threshold, repeating a process of searching and connecting all of points, which are greater than the upper threshold.

5. The clustering algorithm-based multi-parameter cumulative calculation method for the lower limb vascular calcification indexes according to claim 4, wherein the method of fitting by the segmented ellipse is as follows:

step 4.2.1, randomly segmenting an obtained contour into n segments;

step 4.2.2, randomly selecting 12 non-repetitive points in each of segments of the contour, and using a least squares method to fit n candidate ellipses; and step 4.2.3, setting a judgment threshold value $l_0$, comparing a distance $l_i$ between the point ($x_i$, $y_i$) and a candidate ellipse contour with the judgment threshold value $l_0$; if the distance $l_i$, is greater than the judgment threshold value $l_0$, discarding the changed point and not recording; if the distance $l_i$, is smaller than or equal to the judgment threshold value $l_0$, keeping the changed point, recording as one, and summarizing parameters of the changed point to obtain a data set $V_i$=($x_{ic},y_{ic},a_i,b_i,\theta_i,n_i,s_i$), where a circle center of a candidate ellipse is ($x_{ic}$, $y_{ic}$), a semi-major axis is $a_i$, a semi-minor axis is $b_i$, a rotation angle is $\theta_i$, $s_i$ represents a serial number of each of the segments, and $n_i$ is a number of contour segments; and repeating an above comparison process until all of the points on the candidate ellipse contour are compared, summing up all of kept data set of M points to obtain V={$V_i$=($x_{ic},y_{ic},a_i,b_i,\theta_i,n_i,s_i$)|i=1, 2, . . . , M}, where an one with most votes is determined as a candidate circle.

6. The clustering algorithm-based multi-parameter cumulative calculation method for the lower limb vascular calcification indexes according to claim 5, wherein in step 4.3.1, using a snake model to give a 2D parameter closed curve near a region of interest, and by minimizing an energy functional, deforming a closed curve in the image and continuously approximating a target contour, receiving final evolution results as the target contour, and expressing a contour curve energy function as follows:

$$E^*_{snake} = \int_0^1 E_{snake}(v(s))ds = \int_0^1 E_{int}(v(s)) + E_{ext}(v(s))ds$$

wherein, $E_{snake}(v(s))$ is a curve energy, v(s) is a parameter equation of a snake contour, $E_{int}$ is an internal energy of the contour curve, which determines a smoothness and a continuity of a curve; $E_{ext}$ is an energy given to the curve by an outside energy, which makes the curve move towards a characteristic direction of the target contour, and s is an independent variable describing a boundary; and in step 4.3.2, using a least-square circle fitting method to re-fit a circle, and getting a center of the circle through a weighting function of coordinates of the edge points on all of circles, that is, centers (X, Y) of the calcified spots, wherein $$X = \frac{1}{N}\sum_{i=1}^{N} x_i, Y = \frac{1}{N}\sum_{i=1}^{N} y_i$$

and diameters $$D = \frac{2}{N}\sum_{i=1}^{N} \sqrt{(x_i - X)^2 + (y_i - Y)^2}$$

of the calcified spots are calculated, $x_i$ and $y_i$ respectively represent coordinates of the point on contours of the calcified spots, and N is the number of the points on the contours of the calcified spots; and finally getting an area of the calcified spots.

7. The clustering algorithm-based multi-parameter cumulative calculation method for the lower limb vascular calcification indexes according to claim 1, wherein the cumulative correction coefficient $k=k_h*k_w*k_o*k_p$, $k_h$ is a stenosis cumulative score; $k_w$ is a cumulative score of a wall shear stress w of lower extremity arteries; $k_o$ is a cumulative score of an oscillating shear index of the lower extremity arteries; $k_p$ is a cumulative score of a wall shear stress p of the lower extremity arteries;

a cumulative calculation standard for lower extremity arterial stenosis is as follows: according to the lumen area of the lower extremity arteries, it is divided into four grades: I. under lumen diameter reduction of 1%-25%, the stenosis cumulative score $k_h$ is 1 point; II. under lumen diameter reduction of 25%-50%, the stenosis cumulative score $k_h$ is 2 points; III. under lumen diameter reduction 51%-75%, the stenosis cumulative score $k_h$ is 3 points; IV under lumen diameter reduction 76%-100%, the stenosis cumulative score $k_h$ is 4 points, wherein a method of collecting stenosis data is as follows: collecting a maximum value of a vascular stenosis $h_{max}$ and an average value $\bar{h}$ of the stenosis, in a segment with calcified plaques, of the lower extremity artery, and determining a value $\hat{h}$ of vascular stenosis of the segment with calcified plaques according to $\hat{h}=ah_{max}+b\bar{h}$, where a and b are constant coefficients;

the cumulative calculation standard for the wall shear stress w of lower limb arteries is as follows: the wall shear stress in an arterial system is generally (10-70) dynes/cm², and when the wall shear stress w is (0-4) dynes/cm², the cumulative score $k_w$ is 3 points, when the wall shear stress w is (5-10) dynes/cm², the cumulative score $k_w$ is 2 points, and when the wall shear stress w is (11-70) dynes/cm², the cumulative score $k_w$ is 1 point;

an accumulative calculation standard for the oscillating shear index of the lower limb arteries is as follows: a normal range of the oscillating shear index of the lower limb arteries is 0-0.5, when the oscillating shear index is lower than 0.2, the cumulative score $k_o$ is 3 points, when the oscillating shear index is between 0.2 and 0.3, the cumulative score $k_o$ is 2 points, and when the oscillating shear index is between 0.3 and 0.5, the cumulative score $k_o$ is 1 point;

the accumulative calculation standard for the wall shear stress p of the lower limb arteries is as follows: a normal range of indicators is a systolic blood pressure of 90-140 mmHg, a diastolic blood pressure of 60-90 mmHg; when the systolic blood pressure is lower than 90 mmHg and the diastolic blood pressure is lower than 60 mmHg, the cumulative score $k_p$ is 3 points; when the systolic blood pressure is between 90-140 mmHg and the diastolic blood pressure is between 60-90 mmHg, the cumulative score $k_p$ is 2 points; and when the systolic blood pressure is higher than 140 mmHg and the diastolic blood pressure is higher than 90 mmHg, the cumulative score $k_p$ is 1 point.

* * * * *